United States Patent
Xiao et al.

(10) Patent No.: US 12,419,554 B2
(45) Date of Patent: Sep. 23, 2025

(54) PRECISE ARTERIAL BLOOD SAMPLING DEVICE

(71) Applicant: GUANGDONG PROVINCIAL HOSPITAL OF CHINESE MEDICINE, Guangzhou (CN)

(72) Inventors: Yingchao Xiao, Guangzhou (CN); Zhiqiang Chen, Guangzhou (CN); Jiechao Xiao, Guangzhou (CN)

(73) Assignee: GUANGDONG PROVINCIAL HOSPITAL OF CHINESE MEDICINE, Guangzhou (CN)

( * ) Notice: Subject to any disclaimer, the term of this patent is extended or adjusted under 35 U.S.C. 154(b) by 500 days.

(21) Appl. No.: 18/105,886

(22) Filed: Feb. 6, 2023

(65) Prior Publication Data

US 2023/0172503 A1 Jun. 8, 2023

Related U.S. Application Data

(63) Continuation of application No. PCT/CN2021/100240, filed on Jun. 16, 2021.

(30) Foreign Application Priority Data

Jun. 19, 2020 (CN) .......................... 202021142357.0

(51) Int. Cl.
*A61B 5/15* (2006.01)
*A61B 5/153* (2006.01)

(52) U.S. Cl.
CPC .... *A61B 5/150748* (2013.01); *A61B 5/15003* (2013.01); *A61B 5/153* (2013.01)

(58) Field of Classification Search
CPC .......... A61B 5/150748; A61B 5/15003; A61B 5/153; A61B 5/14503; A61B 5/150587; A61B 5/150717
See application file for complete search history.

(56) References Cited

U.S. PATENT DOCUMENTS 9,743,875 B2 * 8/2017 Maguire ................ A61M 5/427
2009/0099437 A1 * 4/2009 Yuzhakov .......... A61B 5/14532
600/583

(Continued)

FOREIGN PATENT DOCUMENTS

CN 208065183 U 11/2018
CN 109998649 A 7/2019

(Continued)

OTHER PUBLICATIONS

International Search Report issued in corresponding International application No. PCT/CN2021/100240, mailed Oct. 8, 2021.

(Continued)

*Primary Examiner* — Charles A Marmor, II
*Assistant Examiner* — Severo Antonio P Lopez

(57) ABSTRACT

A precise arterial blood sampling device comprising a pen cap and a pen container which comprises a front pen container and a rear pen container, wherein: a first piezoelectric sensor sensing column is horizontally fixed to the front pen container, a horizontal slide rail is provided on the front pen container, a second piezoelectric sensor sensing column is provided on the horizontal slide rail, splines are provided on the second piezoelectric sensor sensing column, an elongated groove is formed on the front pen container, and a sensing column extending/retracting control wheel fitting with the splines is provided in the elongated groove; and a control chip, a needle ejection mechanism, a display screen, and a switch are provided inside the rear pen container, and the first piezoelectric sensor sensing column, the second piezoelectric sensor sensing column and the display screen are connected to the control chip respectively.

8 Claims, 3 Drawing Sheets

(56) References Cited

U.S. PATENT DOCUMENTS

2015/0065916 A1    3/2015  Maguire et al.
2018/0028765 A1*   2/2018  Waller ................ A61M 5/3202
2018/0132781 A1    5/2018  Weli Numbere

FOREIGN PATENT DOCUMENTS

CN    209474630 U    10/2019
CN    110840464 A     2/2020
WO   2017171827 A1   10/2017

OTHER PUBLICATIONS

Written Opinion of the International Searching Authority for No. PCT/CN2021/100240.

* cited by examiner

PRECISE ARTERIAL BLOOD SAMPLING DEVICE

DETAILED APPLICATION

The present disclosure is proposed upon and claims the priority of Chinese patent application No. 202021142357.0, filed on Jun. 19, 2020, the contents of which are incorporated herein by reference in its entirety.

TECHNICAL FIELD

The present invention relates to a blood sampling device, in particular to a precise arterial blood sampling device.

BACKGROUND ART

Blood gas analysis can reflect the respiratory and metabolic functions of the body, monitor acid-base balance, hypoxia, carbon dioxide retention and electrolyte, determine acute and chronic respiratory failure and disease progression, and provide basis for disease diagnosis. Arterial blood sampling is usually required before blood gas analysis, and can be implemented by puncturing a radial artery, femoral artery, brachial artery or dorsalis pedis artery.

At present, in the process of collecting an arterial blood gas sample clinically, the commonly used method relies on subjective clinical experience of an operator to select an appropriate artery and an appropriate angle, touch the strongest pulse of the artery and insert a needle. However, the clinical experience of artificially touching the strongest pulse and inserting the needle is highly subjective and less accurate. In particular, a junior operator may puncture a vein mistakenly or fail in puncture, making it difficult to collect a sample by one puncture. As a result, repeated puncture is required. The repeated puncture easily causes a series of problems such as vascular injury, subcutaneous hemorrhage, arterial spasm, and pseudoaneurysm, and even causes compartment syndrome, which increases the pain and complications of patients. In addition, when the operation does not succeed, a complete set of operating device needs to be replaced, resulting in waste of resources and increase of medical expenses. Therefore, the subjective clinical experience of an operator can hardly meet higher clinical use needs in the prior art. At present, a precise arterial blood sampling device is clinically urgently needed to quickly determine the position of an artery and accurately puncture the artery.

SUMMARY

In order to solve the above problems, the present invention provides a precise arterial blood sampling device.

A precise arterial blood sampling device includes a pen cap and a pen container which are movably connected, the pen container includes a front pen container and a rear pen container which are movably connected, wherein:

A first piezoelectric sensor sensing column is horizontally fixed to the lower end of the interior of the front pen container, a horizontal slide rail is provided on the upper part of the interior of the front pen container, a second piezoelectric sensor sensing column is provided on the horizontal slide rail, splines are provided on the upper end of the second piezoelectric sensor sensing column, an elongated groove is formed on the external top wall of the front pen container, and a sensing column extending/retracting control wheel fitting with the splines is provided in the elongated groove;

A control chip, a needle ejection mechanism, a display screen, and a switch are provided inside the rear pen container, the needle ejection mechanism is fixed inside the rear pen container, the switch is connected to the control chip, and the first piezoelectric sensor sensing column, the second piezoelectric sensor sensing column and the display screen are connected to the control chip respectively.

Further, a visible window is provided on the outer wall of the rear pen container facing the needle ejection mechanism.

Further, the needle ejection mechanism is provided at the front end of the interior of the rear pen container, the needle ejection mechanism includes a needle mechanism and an ejection mechanism, and the needle mechanism is detachably connected to the ejection mechanism; the ejection mechanism includes a bevel, a first resilient part, a Y-shaped fork handle, an ejection switch connecting rod, a fulcrum, and a second resilient part; the Y-shaped fork handle is detachably connected to the needle mechanism, the bevel is fixed inside the rear pen container, one end of the first resilient part is connected to the bevel, the other end of the first resilient part is connected to the Y-shaped fork handle, and the Y-shaped fork handle is movably connected to the ejection switch connecting rod; and the rear end of the ejection switch connecting rod is connected to the rear pen container by means of the fulcrum, the bottom of the front end of the ejection switch connecting rod is connected to the upper end of the second resilient part, the lower end of the second resilient part is fixedly connected to the lower wall of the rear pen container, an upward protruded bayonet is provided at the top of the front end of the ejection switch connecting rod, and an ejection switch is provided at the tail end of the ejection switch connecting rod.

Further, the needle mechanism includes a blood sampling needle, a blood sampling vessel, and a base, wherein the blood sampling needle is in communication with the blood sampling vessel and is fixed on the base.

Further, a rectangular groove is formed on the outer wall of the front pen container, the tail end of the rectangular groove is close to the tail end of the front pen container, a needle macro adjustment knob is provided on the outer wall of the base, and the needle macro adjustment knob is placed in the rectangular groove.

Further, a stop rope is provided in the rectangular groove, one end of the stop rope is fixed to the bottom of the most front end of the rectangular groove, and the other end is movably connected to the upper of the front part of the rectangular groove.

Further, a plurality of fixing columns are provided at the upper part of the rectangular groove, one end of the stop rope is fixed to the bottom of the most front end of the rectangular groove, and the other end is movably wound on the fixing columns.

Further, scale values are provided at the lower of the front end of the rectangular groove.

Compared with the prior art, the present invention achieves the following beneficial effects: In the present invention, arterial pulsation is precisely measured by the combination of the first piezoelectric sensor sensing column and the second piezoelectric sensor sensing column, and an optimal blood sampling needle penetration point is determined by the measured arterial pulsation to replace existing needle penetration by the experience of medical staff, which can ensure needle penetration accuracy, ensure a blood sampling effect, and improve nursing comfort of patients.

BRIEF DESCRIPTION OF THE DRAWINGS

In order to describe the technical solutions in embodiments of the present invention or in the prior art more clearly, the drawings which need to be used in the description of the embodiments or the prior art will be simply introduced below. Apparently, the accompanying drawings in the following description show merely some embodiments of the present invention, and those of ordinary skill in the art may still derive other drawings according to these drawings without any creative efforts.

Figure 1:
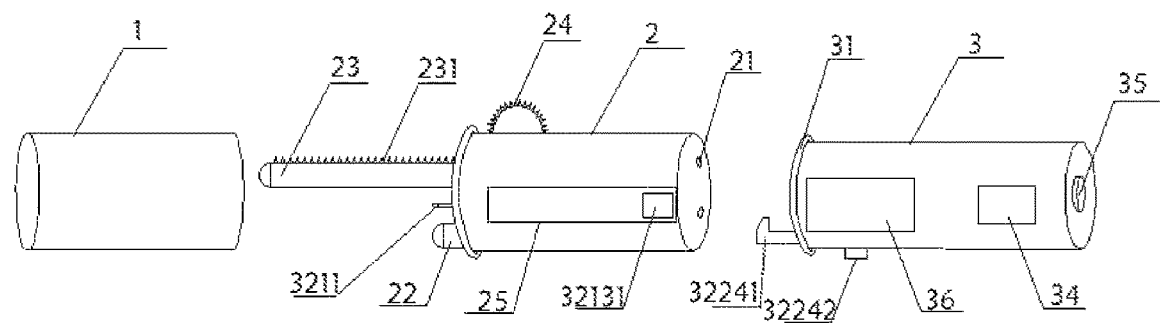
FIG. 1 is a structural schematic diagram of an embodiment of the present invention.
Figure 2:
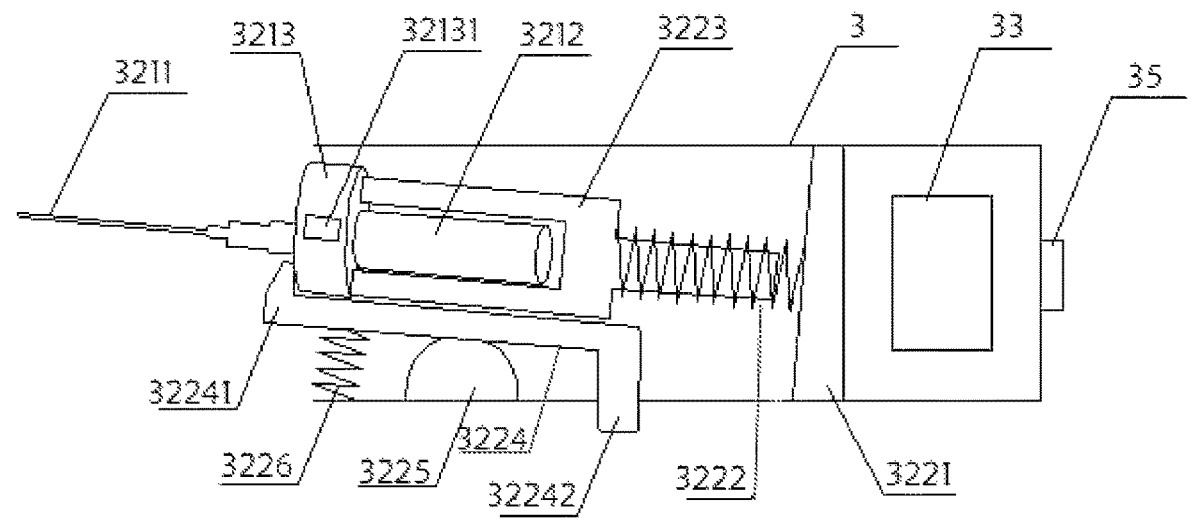
FIG. 2 is a schematic diagram of an internal structure of a rear pen container in an embodiment of the present invention.
Figure 3:
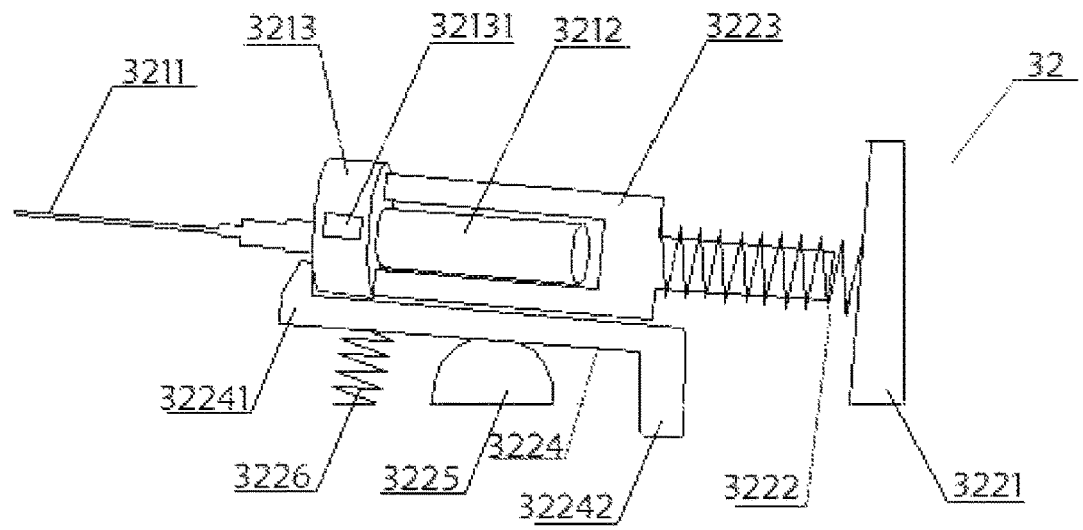
FIG. 3 is a structural schematic diagram of a needle ejection mechanism in an embodiment of the present invention.
Figure 4:
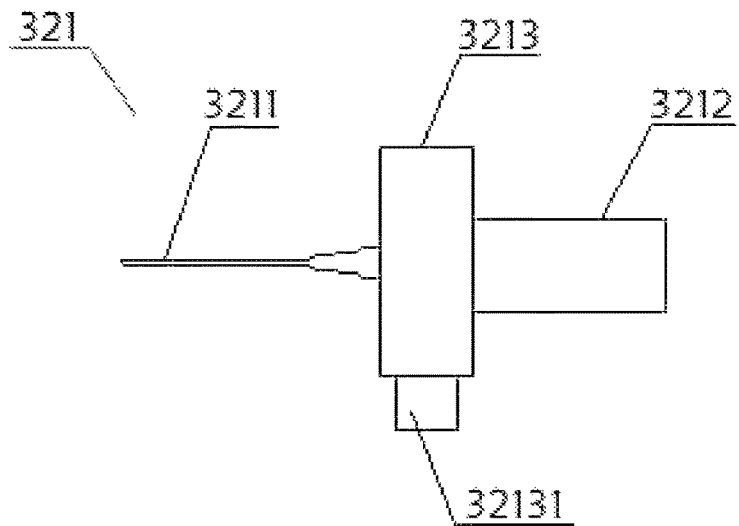
FIG. 4 is a structural schematic diagram of a needle mechanism in an embodiment of the present invention.
Figure 5:
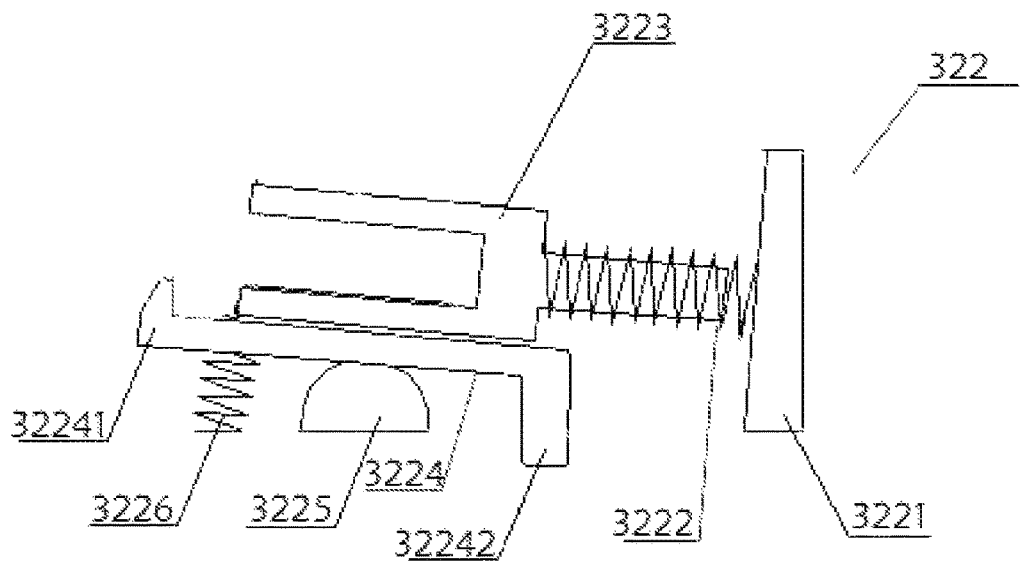
FIG. 5 is a structural schematic diagram of an ejection mechanism in an embodiment of the present invention.

In the figures, 1—pen cap, 2—front pen container, 21—small dotted protrusion, 22—first piezoelectric sensor sensing column, 23—second piezoelectric sensor sensing column, 231—spline, 24—extending/retracting control wheel, 25—rectangular groove, 251—stop rope, 252—fixing column, 253—scale value, 3—rear pen container, 31—small arc protrusion, 32—needle ejection mechanism, 321—needle mechanism, 3211—blood sampling needle, 3212—blood sampling vessel, 3213—base, 32131—needle macro adjustment knob, 322—ejection mechanism, 3221—bevel, 3222—first resilient part, 3223—Y-shaped fork handle, 3224—ejection switch connecting rod, 32241—bayonet, 32242—ejection switch, 3225—fulcrum, 3226—second resilient part, 33—control chip, 34—display screen, 35—switch, 36—visible window.

DETAILED DESCRIPTION OF THE EMBODIMENTS

The technical solutions in the embodiments of the present invention will be clearly and completely described with reference to the accompanying drawings in the present invention. Apparently, the described embodiments are merely some of, not all of the embodiments of the present invention. All other embodiments obtained by those of ordinary skill in the art based on the embodiments of the present invention without any creative effort shall fall within the protection scope of the present invention.

As shown in FIGS. 1-5, as an embodiment of the present invention, a precise arterial blood sampling device includes a pen cap 1, a front pen container 2, and a rear pen container 3, all three are cylindrical and hollow and are movably connected. Specifically, a circle of smooth small arc protrusions 31 are provided on the outer wall of the most front end of the rear pen container 3, and smooth small dotted protrusions 21 are uniformly provided on the circumferential inner wall of the tail end of the front pen container 2. The small arc protrusions 31 may enter and exit the small dotted protrusions 21 under the condition of manual force to connect the front pen container 2 and the rear pen container 3 movably, and the pen cap 1 and the front pen container 2 may also be connected in the same way. As another implementation manner of this embodiment, the pen cap 1, the front pen container 2 and the rear pen container 3 may also be movably connected by threads. A first piezoelectric sensor sensing column 22 is horizontally fixed to the lower inner wall of the front pen container 2, a horizontal slide rail (not shown) is provided on the upper inner wall of the front pen container 2, a second piezoelectric sensor sensing column 23 is provided on the horizontal slide rail, splines 231 are horizontally and uniformly provided on the upper end of the second piezoelectric sensor sensing column 23, an elongated groove (not shown) is formed on the external top wall of the front pen container 2, a sensing column extending/retracting control wheel 24 fitting with the splines 231 is provided in the elongated groove, and the sensing column extending/retracting control wheel 24 can be rolled to adjust the length of the second piezoelectric sensor sensing column 23 exposed to the front pen container 2. The present invention uses the combination of the first piezoelectric sensor sensing column 22 and the second piezoelectric sensor sensing column 23 to detect arterial pulsation of a blood sampled person, which can ensure the accuracy of detection results. A needle ejection mechanism 32, a control chip 33, a display screen 34, and a switch 35 are provided inside the rear pen container 3. The needle ejection mechanism 32 is fixed inside the rear pen container 3, the needle ejection mechanism 32 can eject a needle, and the ejected needle enters the human body to collect blood. The switch 35 is connected to the control chip 33 to control the working state of the chip 33, the switch 35 is located at the tail end of the rear pen container 3, the display screen 34 is provided on the outer wall of the rear pen container 3, and the first piezoelectric sensor sensing column 22, the second piezoelectric sensor sensing column 23, and the display screen 34 are connected to the control chip 33 respectively. The first piezoelectric sensor sensing column 22 and the second piezoelectric sensor sensing column 23 are used for detecting pulsation of the human body and transmitting detection results to the control chip 33, and the control chip 33 controls the display screen 34 to display arterial pulsation values of the human body detected by the first piezoelectric sensor sensing column 22 and the second piezoelectric sensor sensing column 23. Specifically, the control chip 33 may be a STM8S103f3 chip available in the market, the display screen 34 is an LED display screen, and the first piezoelectric sensor sensing column 22 and the second piezoelectric sensor sensing column 23 may be SS-GFC piezoelectric sensors produced by E-TOUCH Company available in the market, with specifications: Ag electrode, 13 mm*24 mm rectangle, and ultra-thin package.

Further, the needle ejection mechanism 32 is provided in the front of the rear pen container 3, the needle ejection mechanism 32 includes a needle mechanism 321 and an ejection mechanism 322, and the needle mechanism 321 and the ejection mechanism 322 are detachably connected. The ejection mechanism 322 includes a bevel 3221, a first resilient part 3222, a Y-shaped fork handle 3223, an ejection switch connecting rod 3224, a fulcrum 3225, and a second resilient part 3226. The Y-shaped fork handle 3223 is detachably connected to the needle mechanism 321, the bevel 3221 is fixed inside the rear pen container 3, one end of the first resilient part 3222 is connected to the bevel 3221, the bevel 3221 is used for supporting the first resilient part 3222, the other end of the first resilient part 3222 is connected to the Y-shaped fork handle 3223, and the Y-shaped fork handle 3223 is movably connected to the ejection switch connecting rod 3224. The rear end of the ejection switch connecting rod 3224 is connected to the rear pen container 3 by means of the fulcrum 3225, the bottom of the front end of the ejection switch connecting rod 3224 is connected to the upper end of the second resilient part 3226, the lower end of the second resilient part 3226 is fixedly connected to the lower wall of the rear pen container 3, an upward protruded bayonet 32241 is provided at the top of the front end of the ejection switch connecting rod 3224, the bayonet 32241 is used for fixing the needle mechanism 321 provided on the Y-shaped fork handle 3223, an ejection switch 32242 is provided at the tail end of the ejection switch connecting rod 3224, and the ejection switch 32242 is used for controlling the ejection of the needle mechanism 321. When the needle mechanism 321 needs to be ejected, the ejection switch 32242 is started, the ejection switch connecting rod 3224 compresses the second resilient part 3226 downward, the bayonet 32241 moves down to release the needle mechanism 321, and the needle mechanism 321 is ejected by the resilient force of the first resilient part 3222.

Further, the needle mechanism 321 includes a blood sampling needle 3211, a blood sampling vessel 3212, and a base 3213. The blood sampling needle 3211 is in communication with the blood sampling vessel 3212 and is fixed by the base 3213 at the communication place. When the needle mechanism 321 is mounted on the Y-shaped fork handle 3223, the bayonet 32241 holds the base 3213 to fix the needle mechanism 321.

Further, a rectangular groove 25 is formed on the outer wall of the front pen container 2, and the tail end of the rectangular groove 25 is close to the tail end of the front pen container 2. The needle mechanism 321 includes a disposable blood sampling needle 3211, a blood sampling vessel 3212, and a base 3213. The disposable blood sampling needle 3211 is in communication with the blood sampling vessel 3212 and is fixed by the base 3213 at the communication place. A needle macro adjustment knob 32131 is provided on the outer wall of the base 3213, and the needle macro adjustment knob 32131 is placed in the rectangular groove 25. The rectangular groove 25 can restrain an ejection track of the needle mechanism, so as to avoid adverse response caused by the rapid insertion of the needle into the human body when the operator exerts too much force.

Further, a visible window 36 is provided on the outer wall of the rear pen container 3 facing the needle ejection mechanism 32. The visible window 36 may be used for observing the blood sampling amount, which provides an effective means for controlling the blood sampling amount.

Figure 6:
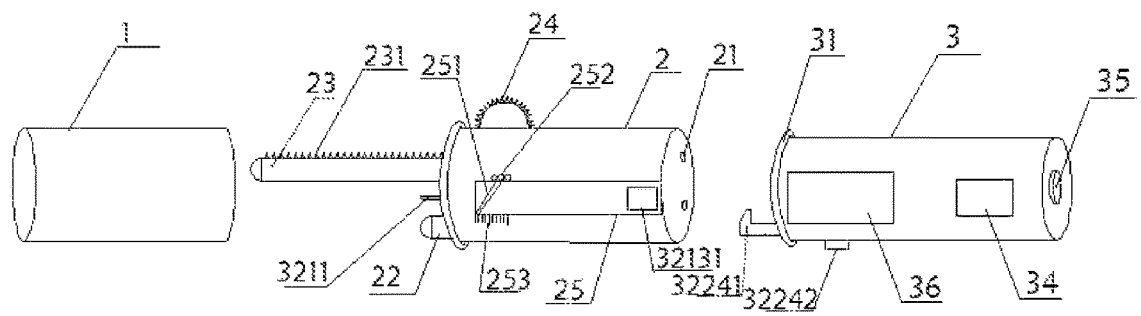
FIG. 6 is a structural schematic diagram of a preferred embodiment of the present invention.

Preferably, as shown in FIG. 6, a stop rope 251 is provided in the rectangular groove 25, one end of the stop rope 251 is fixed to the bottom of the most front end of the rectangular groove 25, and the other end of the stop rope 251 is movably connected to the upper of the front part of the rectangular groove 25. Specifically, a plurality of fixing columns 252 are provided at the upper of the rectangular groove 25, and the other end of the stop rope 251 is movably wound on the fixing columns 252. The plurality of fixing columns 252 have the same horizontal height and are provided in the ejection direction of the needle mechanism 321. When the precise arterial blood sampling device is used, the stop rope 251 can be wound on different fixing columns as required.

Preferably, scale values 253 are provided at the lower of the front end of the rectangular groove 25. According to the adjustment position of the stop rope, the scale values 253 can display length scales of needle ejection.

When the precise arterial blood sampling device provided by the present invention does not work, the pen cap 1, the front pen container 2 and the rear pen container 3 of a blood sampling pen are connected, and the needle mechanism 321 is not placed therein, such that the parts of the blood sampling device can be protected in the pen container from damage.

Figure 7:
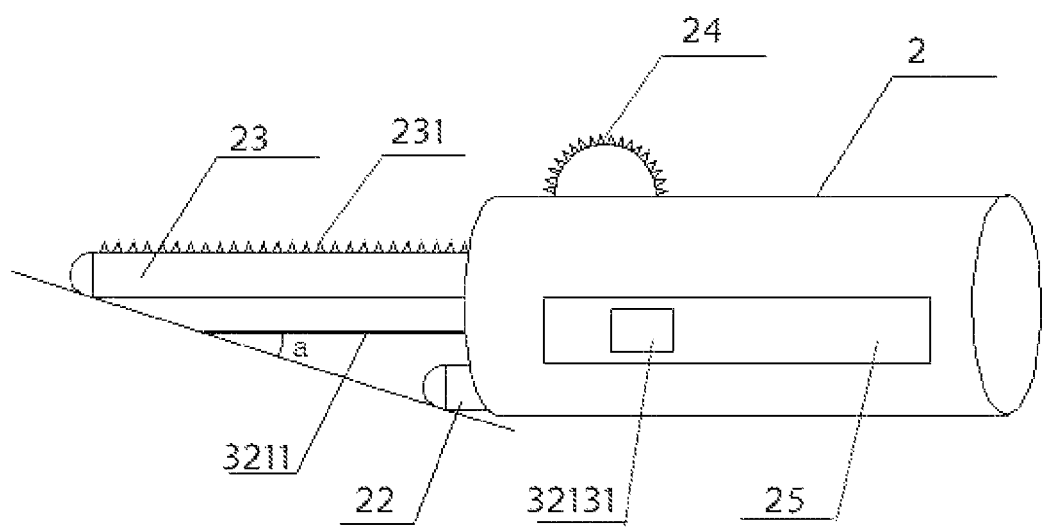
FIG. 7 is a schematic diagram of a needle penetration angle in an embodiment of the present invention.

In the blood sampling process, the pen cap 1 and the rear pen container 3 of the blood sampling pen are first removed, and the sensing column extending/retracting control wheel 24 is adjusted, such that the angle formed by the second piezoelectric sensor sensing column 23 and the first fixed piezoelectric sensor sensing column 22 is suitable for a blood sampling angle. Generally speaking, as shown in FIG. 7, the connection of the blood sampling needle 3211 with the second piezoelectric sensor sensing column 23 and the first piezoelectric sensor sensing column 22 forms an angle α, which is suggested to be 10-30° for radial artery blood sampling and 90° for femoral artery blood sampling. The needle mechanism 321 is placed in the Y-shaped fork handle 3223 of the ejection mechanism 322 and fixed by the bayonet 32241 of the ejection switch connecting rod 3224. Then, the front pen container 2 and the rear pen container 3 are connected, the needle macro adjustment knob 32131 of the needle mechanism 321 is placed in the rectangular groove 25 on the outer wall of the front pen container 2, and the blood sampling vessel of the needle mechanism 321 can be seen through the visible window 36 of the rear pen container 3. Next, the switch 35 at the tail end of the rear pen container 3 is pressed. After the display screen 34 on the rear pen container 3 displays "Ready", the blood sampling device is slowly moved to continuously detect a pulsation area of a radial artery or femoral artery. When the display screen 34 displays "Start", that is, an optimal blood sampling point is detected out, the second piezoelectric sensor sensing column 23 and the first fixed piezoelectric sensor sensing column 22 are maintained unmovable. The ejection switch 33342 at the bottom of the rear pen container 3 is pressed to start the ejection mechanism 322, and the ejection mechanism 322 penetrates the blood sampling needle 3211 into the artery. The needle penetration is observed. If necessary, the needle macro adjustment knob may be slightly moved to adjust the needle penetration depth. The blood sampling amount in the blood sampling vessel 3212 is observed from the visible window of the rear pen container 3. When the required blood volume is collected, the blood sampling needle 3211 can be pulled out. The blood sampling needle and the blood sampling vessel are pulled out to complete blood sampling. Specifically, the control chip 33 receives pulsation values detected by the second piezoelectric sensor sensing column 23 and the first fixed piezoelectric sensor sensing column 22, and controls the display screen 34 according to a preset determination rule to display an instruction. The preset determination rule is that, when the control chip 33 is started, the control chip 33 controls the display screen to display a "Ready" signal, and the control chip 33 receives and determines data detected by the second piezoelectric sensor sensing column 23 and the first fixed piezoelectric sensor sensing column 22; and when the control chip 33 determines that the data detected by the second piezoelectric sensor sensing column 23 and the first fixed piezoelectric sensor sensing column 22 are identical and not zero, the control chip 33 controls the display screen 34 to display a "Start" signal.

To sum up, the present invention provides a precise arterial blood sampling device, which reduces mistaken penetration of the blood sampling needle into a vein or puncture failure caused by misoperation during artificial blood sampling, and relieves blood sampling pains for patients.

The present invention is further described above by virtue of specific embodiments, but it should be appreciated that the specific description here shall not be understood as limitations to the essence and scope of the present invention. Various modifications made to the above embodiments by those of ordinary skill in the art after reading the description shall fall within the protection scope of the present invention.

The invention claimed is:

1. A precise arterial blood sampling device, comprising a pen cap and a pen container which are movably connected, in which the pen container comprises a front pen container and a rear pen container which are movably connected, wherein:

a first piezoelectric sensor sensing column is horizontally fixed to a lower end of an interior of the front pen container, a horizontal slide rail is provided on an upper part of the interior of the front pen container, a second piezoelectric sensor sensing column is provided on the horizontal slide rail, splines are provided on an upper end of the second piezoelectric sensor sensing column, an elongated groove is formed on an external top wall of the front pen container, and a sensing column extending/retracting control wheel fitting with the splines of the second piezoelectric sensing column is provided in the elongated groove, wherein the sensing column extending/retracting control wheel is configured to rotate to adjust a length of the second piezoelectric sensing column extending from the front pen container, such that the first piezoelectric sensing column and the second piezoelectric column are configurable to form a suitable blood sampling angle; and wherein a control chip, a needle ejection mechanism, a display screen, and a switch are provided inside the rear pen container, the needle ejection mechanism is fixed inside the rear pen container, the switch is connected to the control chip, and the first piezoelectric sensor sensing column, the second piezoelectric sensor sensing column and the display screen are connected to the control chip respectively.

2. The precise arterial blood sampling device according to claim 1, wherein a visible window is provided on an outer wall of the rear pen container facing the needle ejection mechanism.

3. The precise arterial blood sampling device according to claim 1, wherein the needle ejection mechanism is provided at a front end of an interior of the rear pen container, the needle ejection mechanism comprises a needle mechanism and an ejection mechanism, and the needle mechanism is detachably connected to the ejection mechanism;

wherein the ejection mechanism comprises a bevel, a first resilient part, a Y-shaped fork handle, an ejection switch connecting rod, a fulcrum, and a second resilient part;

wherein the Y-shaped fork handle is detachably connected to the needle mechanism, the bevel is fixed inside the rear pen container, one end of the first resilient part is connected to the bevel, an other end of the first resilient part is connected to the Y-shaped fork handle, and the Y-shaped fork handle is movably connected to the ejection switch connecting rod; and wherein a rear end of the ejection switch connecting rod is connected to the rear pen container by means of the fulcrum, a bottom of a front end of the ejection switch connecting rod is connected to an upper end of the second resilient part, a lower end of the second resilient part is fixedly connected to a lower wall of the rear pen container, an upward protruded bayonet is provided at a top of the front end of the ejection switch connecting rod, and an ejection switch is provided at a tail end of the ejection switch connecting rod.

4. The precise arterial blood sampling device according to claim 3, wherein the needle mechanism comprises a blood sampling needle, a blood sampling vessel, and a base, the blood sampling needle is in communication with the blood sampling vessel and is fixed on the base.

5. The precise arterial blood sampling device according to claim 4, wherein a rectangular groove is formed on an outer wall of the front pen container, a tail end of the rectangular groove is close to a tail end of the front pen container, a needle macro adjustment knob is provided on an outer wall of the base, and the needle macro adjustment knob is placed in the rectangular groove.

6. The precise arterial blood sampling device according to claim 5, wherein a stop rope is provided in the rectangular groove, one end of the stop rope is fixed to a bottom of a most front end of the rectangular groove, and an other end of the stop rope is movably connected to an upper of a front part of the rectangular groove.

7. The precise arterial blood sampling device according to claim 6, wherein a plurality of fixing columns are provided at an upper of the rectangular groove, one end of the stop rope is fixed to the bottom of the most front end of the rectangular groove, and the other end of the stop rope is movably wound on the plurality of fixing columns.

8. The precise arterial blood sampling device according to claim 6, wherein scale values are provided at the lower of the front end of the rectangular groove.

* * * * *